(12) United States Patent
Hagan

(10) Patent No.: US 9,844,395 B2
(45) Date of Patent: Dec. 19, 2017

(54) UMBRELLA INFERIOR VENA CAVA FILTER RETRIEVAL DEVICE

(71) Applicant: COOK MEDICAL TECHNOLOGIES LLC, Bloomington, IN (US)

(72) Inventor: David Hagan, Bloomington, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 210 days.

(21) Appl. No.: 14/199,473

(22) Filed: Mar. 6, 2014

(65) Prior Publication Data
US 2014/0277086 A1   Sep. 18, 2014

Related U.S. Application Data

(60) Provisional application No. 61/783,939, filed on Mar. 14, 2013.

(51) Int. Cl.
| | |
|---|---|
| *A61M 29/00* | (2006.01) |
| *A61B 17/50* | (2006.01) |
| *A61F 2/01* | (2006.01) |
| *A61B 17/22* | (2006.01) |

(52) U.S. Cl.
CPC .............. *A61B 17/50* (2013.01); *A61F 2/01* (2013.01); *A61B 2017/22035* (2013.01); *A61F 2002/011* (2013.01); *A61F 2002/016* (2013.01); *A61F 2230/0093* (2013.01)

(58) Field of Classification Search
CPC . A61B 17/50; A61B 17/221; A61B 17/32056; A61B 2017/22035; A61B 2002/001; A61B 2017/2212; A61B 2017/2215; A61B 2017/2217; A61B 2017/22034; A61F 2/01; A61F 2/95; A61F 2/013; A61F 2002/011
USPC .......... 606/200, 127, 108, 198, 113–114, 128
See application file for complete search history.

(56) References Cited

U.S. PATENT DOCUMENTS

| | | | |
|---|---|---|---|
| 5,769,816 A * | 6/1998 | Barbut ................ | A61F 2/013 604/93.01 |
| 5,941,896 A * | 8/1999 | Kerr .................... | A61F 2/01 606/192 |
| 6,342,062 B1 | 1/2002 | Suon et al. | |
| 6,726,621 B2 | 4/2004 | Suon et al. | |

(Continued)

*Primary Examiner* — Jonathan Miles
*Assistant Examiner* — Majid Jamialahmadi
(74) *Attorney, Agent, or Firm* — Brinks Gilson & Lione

(57) ABSTRACT

A device for retrieval of a vena cava filter is provided. The retrieval device has, approximately, an umbrella shape and consists of a central shaft; a plurality of frame struts, attached to frame strut attachment points on the central shaft and disposed radially about the central shaft; and a plurality of snare wires. The retrieval device has a collapsed configuration for insertion and removal from a blood vessel of a patient and an expanded state for capturing an intravascular filter in the blood vessel of the patient. The plurality of snare wires provides multiple points at which a vena cava filter, particularly one that has become misaligned during deployment or treatment, can be caught. The frame struts can be substantially sinusoidal in shape and made of shape memory metal, such as Nitinol. The snare wires can be made of a biocompatible material such as silk, polyester, polypropylene, or nylon.

4 Claims, 3 Drawing Sheets

(56) References Cited

U.S. PATENT DOCUMENTS

| | | | |
|---|---|---|---|
| 7,041,117 B2 | 5/2006 | Suon et al. | |
| 7,749,244 B2 | 7/2010 | Brucheimer et al. | |
| 7,993,362 B2 | 8/2011 | Lowe et al. | |
| 2002/0138094 A1* | 9/2002 | Borillo | A61F 2/013 606/200 |
| 2003/0233117 A1* | 12/2003 | Adams | A61F 2/013 606/200 |
| 2005/0090858 A1* | 4/2005 | Pavlovic | A61F 2/01 606/200 |
| 2007/0162071 A1* | 7/2007 | Burkett | A61F 2/01 606/200 |
| 2007/0167974 A1 | 7/2007 | Cully et al. | |
| 2008/0172082 A1* | 7/2008 | Holzer | A61F 2/013 606/200 |
| 2009/0118760 A1 | 5/2009 | Clausen et al. | |
| 2010/0087908 A1* | 4/2010 | Hilaire | A61F 2/013 623/1.11 |
| 2011/0040321 A1 | 2/2011 | Cartier | |
| 2011/0264106 A1* | 10/2011 | Taube | A61B 17/22031 606/113 |
| 2012/0022578 A1* | 1/2012 | Jantzen | A61F 2/01 606/200 |
| 2012/0035646 A1* | 2/2012 | McCrystle | A61F 2/01 606/200 |
| 2013/0046330 A1* | 2/2013 | McIntosh | A61F 2/013 606/200 |

* cited by examiner

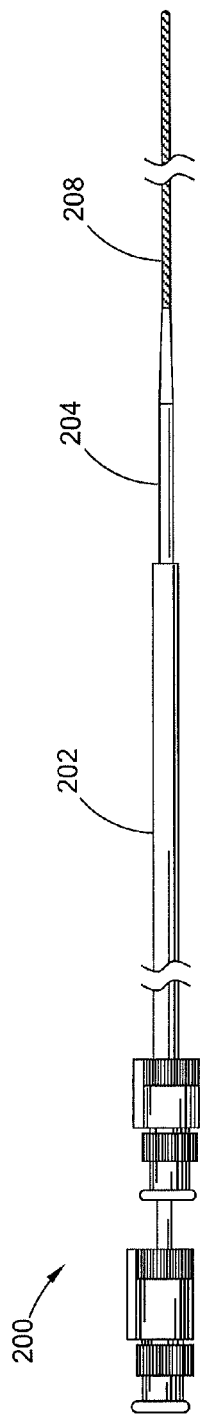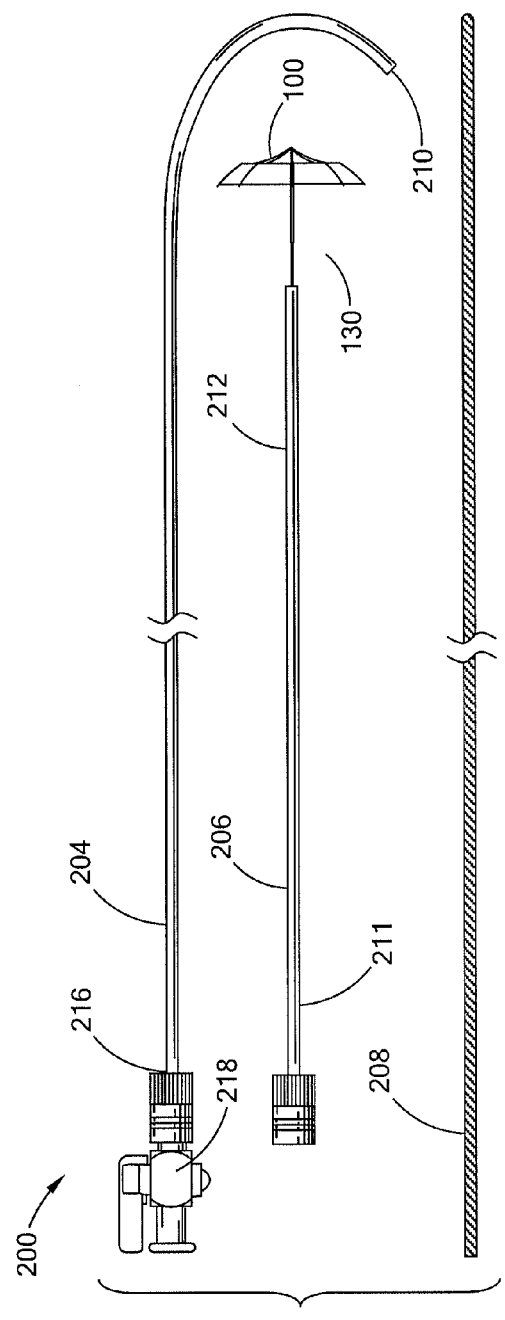

UMBRELLA INFERIOR VENA CAVA FILTER RETRIEVAL DEVICE

CROSS-REFERENCE TO RELATED APPLICATIONS

This application claims the benefit of U.S. Provisional Application No. 61/783,939 filed on Mar. 14, 2013, entitled "UMBRELLA INFERIOR VENA CAVA FILTER RETRIEVAL DEVICE," the entire contents of which are incorporated herein by reference.

BACKGROUND

The present invention relates to medical devices. More particularly, the invention relates to an intravascular filter removal device that can be used to assist in the removal of a filter from the vena cava of a patient.

Filtering devices that are percutaneously placed in the vena cava have been available for a number of years. A need for such filtering devices arises in trauma patients, orthopedic surgery patients, neurosurgery patients, or in patients having medical conditions requiring bed rest or non-movement. Patients having such medical conditions face an increased risk of thrombosis in the peripheral vasculature, wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

Historically, vena cava filters were considered to be permanent implants and remained implanted in the patient for life. More recently, removable vena cava filters have been developed. These filters may be removed from the patient's vena cava after the condition or medical problem that required the device has passed.

A particular problem that can arise during deployment of the filter or during treatment is misalignment of the filter. Many removable vena cava filters are manufactured with a removal hook at their proximal end. A physician or surgeon removing the filter can use a 2D imaging system to guide a looped snare to this hook, snare the hook, dislodge the filter from the vessel wall, and remove the filter from the patient's body.

Removal can be hindered or rendered impossible by minimally invasive means if the filter has become tilted during treatment. A practitioner may not be able to snare the hook of a tilted filter because some portion of the hook may have made contact with the vessel wall and in some cases the vessel may have grown around it. In this case, methods that are less precise and more invasive than simple snaring, such as dislodging the filter with forceps, may have to be employed.

Development of a more elegant means of removing a tilted vena cava filter has proven difficult.

SUMMARY OF INVENTION

The present invention generally provides an intravascular filter removal device suitable for retrieval of a filter from a patient's vena cava, such as via the patient's jugular vein.

While the present invention has been described in terms of certain preferred embodiments, it will be understood that the invention is not limited to the disclosed embodiments, as those having skill in the art may make various modifications without departing from the scope of the following claims. Particular emphasis has been placed on solving the problem of removing a tilted or otherwise misaligned but it will be appreciated that the invention disclosed herein would also be capable of removing a properly-aligned vena cava filter.

In one embodiment, a removal device for an intravascular filter is provided, the device having a collapsed configuration for insertion and removal from a blood vessel of a patient and an expanded state for engaging and capturing an intravascular filter in the vasculature of the patient, the retrieval device comprising a central shaft extending from a first proximal and a first distal end defining a first longitudinal axis; a plurality of struts having a first end and a second end, the second ends being in contact with the central shaft and being disposed radially about the central shaft at substantially the same distance from the distal end of the central shaft along the first longitudinal axis, the distance from the second end to the first end of the struts defining a length of the struts; a plurality of circular connective members connected to each of the struts at points along their lengths substantially equidistant from the central shaft.

In another embodiment, the present invention provides a method of removing an intravascular filter from a vessel of a patient, the method comprising, in a first step, percutaneously inserting a retrieval assembly into a target body vessel, an intravascular retrieval device being positioned in its collapsed configuration and slidably disposed within an interior lumen of the retrieval cannula; in a second step, identifying the location of the filter using visualization technology; in a third step, advancing the retrieval assembly still in its collapsed configuration to a retrieval position proximal to the intravascular filter in the body vessel, the retrieval position being distal to a retrieval hook of the intravascular filter; in a fourth step, expanding the retrieval device into its expanded state; in a fifth step, engaging the retrieval hook of the intravascular filter with a portion of the retrieval device; in a sixth step, returning the retrieval device, still engaged with the retrieval hook, to its collapsed configuration; in a seventh step, withdrawing the retrieval device and the intravascular filter into the interior lumen of the retrieval assembly; and in an eighth step, removing the retrieval assembly and the intravascular filter from the body vessel.

Further objects, features, and advantages of the present invention will become apparent from consideration of the following description and the appended claims when taken in connection with the accompanying drawings.

BRIEF DESCRIPTION OF THE DRAWINGS

The drawings are purely schematic illustrations of various aspects of the invention and are not necessarily to scale, unless expressly stated.

FIG. 3a is a side view of a delivery and retrieval assembly for use with an occlusion device in accordance with some embodiments of the present disclosure and FIG. 3b is an exploded view of the delivery and retrieval assembly of FIG. 3a in accordance with some embodiments of the present disclosure

DETAILED DESCRIPTION

Figure 1E:
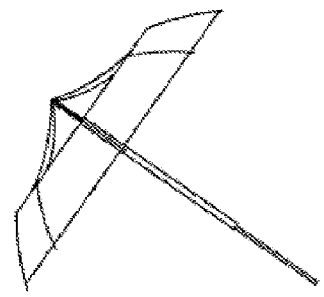
FIG. 1e is a side view of a single strut.

Provided herein is a device for removal of an intravascular filtration device that has been deployed in the vasculature of a patient. The filtration device is generally implanted in order to capture blood clots that may have formed so that they do not travel into portions of the body where their presence may cause damage. Most blood clots form in the lower limbs and are especially problematic if they reach the heart or lungs. As such, many filters are placed in the inferior vena cava, as this vein returns blood from the lower extremities to the heart. However, the device as described can also be used to extract filters from other veins as well.

The type of filters envisioned for removal by this device are roughly cone- or tulip-shaped filters which comprise a plurality of struts that diverge from an apical hub and are configured to engage the vessel wall at their opposite ends. These ends may terminate in hooks or barbs to more firmly engage the vessel wall. The filters are generally collapsible and are deployed percutaneously via catheter.

In some instances, a filter is intended to be implanted permanently; in others, the implantation may be temporary. In the latter case, the filter must be removed from the patient after the danger of embolism has passed. To this end, the filter is usually equipped with a retrieval hook at its apical hub. Using 2D imaging technology, a medical professional can guide retrieval catheter and a snaring wire through the vasculature. The snaring wire usually terminates in a hook of its own, which is used to engage the hook of the filter. The practitioner then frees the filter from the vessel wall and retracts the snaring wire into the retrieval catheter, the filter itself collapsing into the catheter as it is removed.

Retrieval can sometimes be more difficult if the intravascular filter has tilted during the deployment process or over the course of a period of treatment. In these cases, the retrieval hook of the filter can be difficult to access at best or can even have made sufficient contact to have become embedded into the vessel wall, with growth of new tissue around the hook making access impossible. Furthermore, a simple snare with a hook can cause damage if it engages with a part of the filter other than the hook. For instance, if the hook engages with one of the support struts of the filter, there is a possibility that the filter may become even more tilted or that the strut will become damaged by bending or kinking, which may in turn prevent closure or collapse of the filter as removal is attempted.

Due to the danger of bending, kinking, and breakage of the intravascular filter, care must be taken when removing a tilted or misaligned filter. The retrieval hook is the only portion of many of these filters that is designed to keep its structure when a force is applied; it is reinforced such that it can tolerate pushing and prying by the snaring hook, whereas the remainder of the device (that is, the filter body comprised of flexible struts) must be able to expand and collapse for the deployment and retrieval steps. Therefore, rather than risk the damage to the filter by applying excessive force to improper portions of the device, the best solution would be to manipulate the filter in a way that would avoid compromising its structure while regaining access to the retrieval hook.

The device described below can be used to remove a vena cava filter that resides in the vena cava in tilted fashion. One skilled in the art will recognize the advantage of using such a device to remove a tilted vena cava filter but will also note that the removal procedure can be used, with little to no modification, to remove a properly-aligned filter.

As used herein, the term "proximal" means "toward the medical practitioner" and "distal" means "away from the medical practitioner." As a consequence, a filter deployed into the vena cava has its apical hub at its proximal end and its opening at its distal end, and blood flows through the filter from its distal to its proximal end.

FIG. 1 illustrates an umbrella-shaped intravascular retrieval device 10 for removing a tilted vena cava filter. The retrieval device 10 comprises a central shaft 12. The central shaft serves as the force-bearing member of the invention and is preferably made of stainless steel, although other biocompatible materials are also acceptable.

At the distal end of central shaft 12 is a hub region where the frame struts 14 converge. The frame struts 14 are radially disposed about the central shaft, preferably at even increments, and preferably there are 4 to 12 struts associated with the removal device. The frame struts 14 give the device its overall umbrella shape. Each strut has a second end 16 that meets the hub region of the central shaft 12 and a first end 18. The first end 18 is able to move through the vessel in which retrieval is to be attempted so it should be blunted or smoothened to minimize the impact of its contact with a vessel wall.

In contrast to the rigid central shaft 12, the frame struts 14 are flexible. If the struts are made of a similar rigid metal, such as stainless steel, they may gain this flexibility by virtue of hinges where the second ends 16 meet the central shaft 12. In a preferred embodiment, the struts themselves are flexible and are permanently attached to the central shaft 12 at their second ends 16, such as by soldering. The flexibility is by virtue of the material from which they are made; in a preferred embodiment, the memory metal nickel-titanium alloy Nitinol is used to manufacture the frame struts 14. The transition temperature of this Nitinol would allow for easy expansion and collapse of the device while still keeping the overall form. Altogether different materials for the frame struts 14, such as a number of flexible biocompatible plastics, are also contemplated.

Figure 1B:
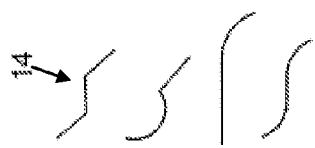
FIGS. 1a-1d are views from various perspectives of an intravascular filter removal device in accordance with the principles of the present invention.

The frame struts 14 can be shaped in a number of ways (see FIG. 1b.) In one embodiment, the struts are simple arcuate structures. In another embodiment, they are sinusoidal, arcing inward toward the central shaft 12 before curving back outward. They can also be made with two or more straight portions formed at angles to one another, so long as the overall shape resembles an umbrella. There may be as few as three struts or as many as up to 24 struts, with six or eight struts representing a preferred embodiment. The struts, if made of memory metal, will be biased into their expanded configuration in order that they will expand when introduced into the target vessel.

Located at intervals along the lengths of the frame struts 14 are the snare wires 19. The snare wires 19 are configured as closed concentric circles around the central shaft 12 and are included with the object of providing multiple surfaces onto which the retrieval hook of an intravascular filter can attach. The illustrated embodiments of FIGS. 1 and 2 are shown with 2 and 3 snare wires, respectively, but embodiments with a single snare wire or four or more snare wires are possible as well.

The frame struts may have ends that are connected to a snare wire 19, or are free of any snare wires.

In a preferred embodiment, the snare wires 19 are made of a material resembling non-resorbable suture thread. Nylon, silk, polyester, and polypropylene are particularly suited to this task, but other biocompatible materials with sufficient strength to support the capture of a filter device are also acceptable. Certain metals, especially flexible alloys like Nitinol, may also be well suited to serving for making snare wires. The diameter of the snare wire is preferably 24 to 40 gauge inclusive, although larger diameters may be practicable in certain circumstances. The snare wires 16 may be attached to the frame struts 14 by melting, tying, or otherwise fusing the materials. They must be attached to the struts 14 in such a way as to support both an expanded and a collapsed configuration.

In another embodiment, the snare wires are not configured to be circular in shape, but rather constitute closed shapes of another configuration, such as triangular, square, rectangular, rhomboid, elliptical, star-shaped, or any other closed shape.

Optionally included are retraction struts 20. Each retraction strut 20 has a first connected end attached to the central shaft 12 proximal to the hub region and a second connected end attached to the frame struts 14 between the first end and the second end. The retraction struts 20, like the frame struts, should be flexible. This flexibility can be imparted by means of hinging or by fabricating the hinges out of memory metal alloys or a suitable biocompatible plastic. Attached to the retraction struts 20 are cords 22 that are pulled in the proximal direction in order to force the retraction struts, which are biased to the expanded configuration, into their collapsed position, and by extension collapsing the frame struts 14 and the entire device 10. When collapsed, the device can then be removed from the vessel of the patient.

Figure 1D:
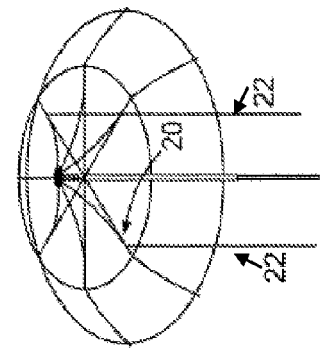
Figure 1A:
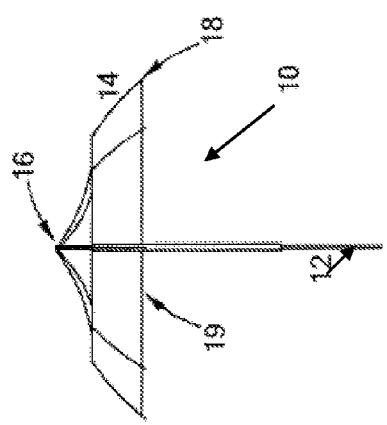
Figure 1C:
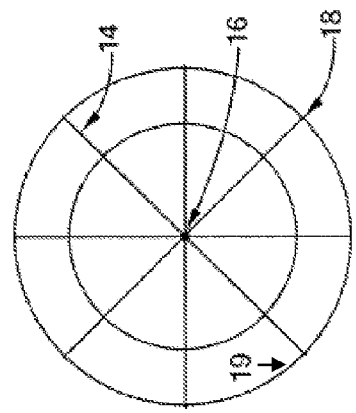

FIG. 1c is a view of the device in its expanded configuration as viewed from its distal end. The illustrated embodiment has eight frame struts 14 and two snare wires 16. FIG. 1d illustrates the same embodiment of the device, this time in a perspective view from the proximal end. From this angle, the retraction struts 20 are visible. FIG. 1e is a side view of the device which more clearly shows the sinusoidal shape of the frame struts 14 of this embodiment.

Figure 2C:
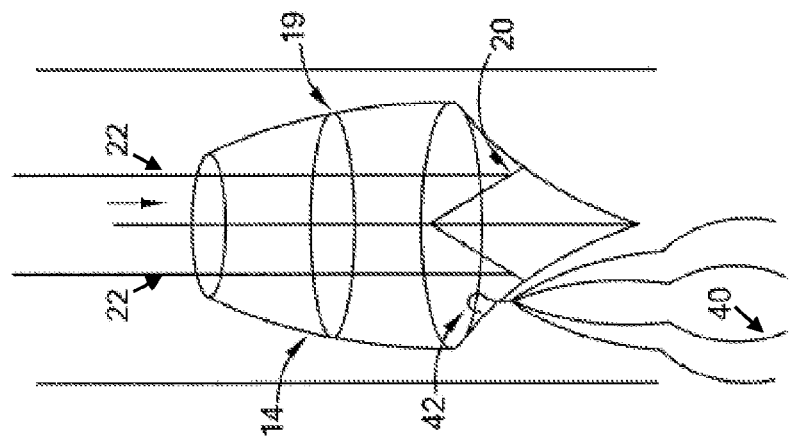
FIGS. 2a-2c are cross-sectional views of the intravascular filter removal device illustrating various steps in the removal of an intravascular filter engaged within the vasculature of a patient.
Figure 2B:
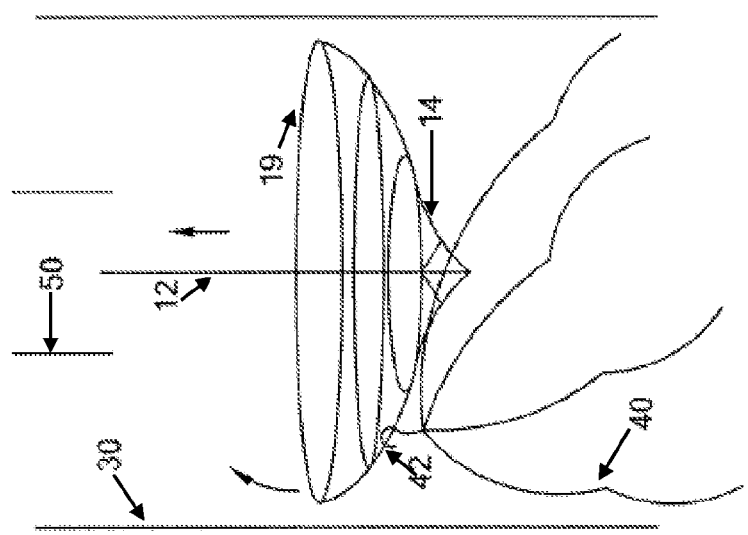
Figure 2A:
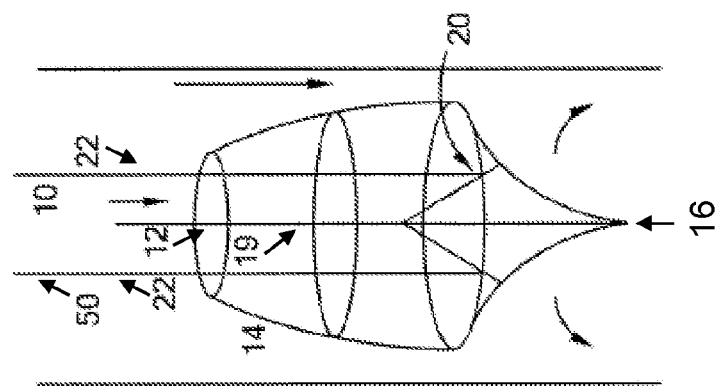

Turning now to FIG. 2a-2c, a multi-step process for engaging and retrieving a tilted vena cava filter is illustrated. The process illustrated encompasses the steps following deployment of the device from within an introducer catheter and concluding with the step preceding withdrawal of the device and the filter from the patient's body. This sequence is not to be considered exclusive or exhaustive as other intermediate steps may be included by practitioners.

General protocols for retrieving a vena cava filter are well known in the art. The first step is generally percutaneous introduction of a catheter in which the retrieval device has been loaded into the body vessel where the filter is located.

FIG. 2a shows retrieval device 10 in its collapsed state within a body vessel 30. Because the frame and retrieval struts are biased into their expanded configurations, the introducer catheter 50 is positioned near the retrieval hook of the filter prior to its extrusion from the catheter lumen. When the umbrella filter removal device moved out of the catheter 50, it is preferable to have at least a portion of the device, preferably including at least one snaring wire, distal to the location of the hook prior to full expansion.

FIG. 2b illustrates an umbrella removal device in its expanded configuration within a vessel 30. This device had been positioned distal to the retrieval hook 42 of vena cava filter 40. The filter 40 is tilted within vessel 30 in a manner that might impede retrieval by conventional means. In the embodiment illustrated, the retrieval hook 42 is engaged with one of the snare wires 16. The purpose of these snare wires is to interact with and catch the hook, but it is also possible that in some cases it would be acceptable for the retrieval hook 42 to engage a frame strut 14 instead. As long as the practitioner was confident that this would not deform either the filter or the retrieval device, and that the return of the retrieval device to its contracted configuration was not impeded, retrieval via frame strut would be acceptable.

FIG. 2c shows the final steps of the retrieval process. Here the cords 20 have been pulled in the proximal direction, in turn causing the retraction struts to move toward the central shaft 12 and collapsing the device. The filter device remains attached to the retrieval device and the two are pulled back into the catheter when they have reached their collapsed state. The catheter system can then be withdrawn from the patient's body and the wound sealed.

FIGS. 3a and 3b depict a delivery assembly 200 for introducing and retrieving the retrieval device 100 for retrieving a filter device from a body cavity in accordance with some embodiments of the present disclosure. However, one skilled in the art will recognize that other delivery assemblies may be used for introducing and retrieving the retrieval device 100 for occluding an opening in a body tissue. As shown, the delivery assembly 200 includes a polytetrafluoroethylene (PTFE) introducer sheath 202 for percutaneously introducing an outer sheath 204 into a body vessel. Of course, any other suitable material for the introducer sheath 202 may be used without falling beyond the scope or spirit of the present invention. The introducer sheath 202 may have any suitable size, for example, between about seven-french to fourteen-french. The introducer sheath 202 serves to allow the outer sheath 204 and an inner member or catheter 206 to be percutaneously inserted to a desired location in the body tissue, cavity or vessel. The inner member may also include, for example, a stylet. The introducer sheath 202 receives the outer sheath 204 and provides stability to the outer sheath 204 at a desired location of the body tissue, cavity or vessel. For example, the introducer sheath 202 is held stationary within the body tissue, cavity or vessel, and adds stability to the outer sheath 204, as the outer sheath 204 is advanced through the introducer sheath 202 into an opening. The outer sheath 204 has a body extending from a proximal end 216 to a distal end 210, the body being tubular and including a sheath lumen extending therethrough.

As shown, the assembly 200 may also include a wire guide 208 configured to be percutaneously inserted within the vasculature to guide the outer sheath 204 to the opening. The wire guide 208 provides the outer sheath 204 with a path to follow as it is advanced within the body tissue, cavity or vessel. The size of the wire guide 208 is based on the inside diameter of the outer sheath 204 and the diameter of the target opening.

When the distal end 210 of the outer sheath 204 is at the desired location within the opening, the wire guide 208 is removed and the retrieval device 100 is inserted into the outer sheath 204. The inner catheter 206 is advanced through the outer sheath 204 for deployment of the retrieval device 100 through the distal end 210 to occlude the opening. The catheter 206 extends from a proximal portion 211 to a distal portion 212 and is configured for axial movement relative to the outer sheath 204. In this example, the distal portion 212 is shown adjacent to the retrieval device 100 before introduction into the outer sheath 204. Thus, before deployment, the retrieval device 100 is coaxially disposed within the lumen of the outer sheath 204 and removably coupled to the distal portion 212 of the catheter 206, or in the alternative, the retrieval device 100 is merely pushed by, but not coupled to, the distal portion 212 of the catheter 206.

The outer sheath 204 further has a proximal end 216 and a hub 218 to receive the inner catheter 206 and retrieval device 100 to be advanced therethrough. The size of the outer sheath 204 is based on the size of the body tissue, cavity vessel in which it percutaneously inserts, the size of the opening, and/or the size of the retrieval device 100.

In this embodiment, the retrieval device 100 and inner catheter 206 are coaxially advanced through the outer sheath 204, following removal of the wire guide 208, in order to position the retrieval device 100 to occlude the opening. The retrieval device 100 is guided through the outer sheath 204 by the inner catheter 206, preferably from the hub 218, and exits from the distal end 210 of the outer sheath 204 at a location within the opening. Thus, the retrieval device 100 is deployable through the distal end 210 of the outer sheath 204 by means of axial relative movement of the catheter 206. In order to more easily deploy the retrieval device 100 into the body vessel, the retrieval device 100 may have a slippery coating, such as silicone or slipcoating.

Likewise, this embodiment may also retrieve the retrieval device 100 by positioning the distal end 210 of the outer sheath 204 adjacent the deployed device 100 in the vasculature. The inner catheter 206 is advanced through the outer sheath 204 until the distal portion 212 protrudes from the distal end 210 of the outer sheath 204. The distal portion 212 is coupled to a proximal end of the retrieval device 100, after which the inner catheter 206 is retracted proximally, drawing the retrieval device 100 into the outer sheath 204.

While the present invention has been described in terms of certain preferred embodiments, it will be understood that the invention is not limited to the disclosed embodiments, as those having skill in the art may make various modifications without departing from the scope of the following claims.

What is claimed is:

1. A method for retrieving an intravascular filter from a vessel of a patient, the method comprising:
   percutaneously inserting a retrieval assembly into a target body vessel, an intravascular retrieval device being positioned in its collapsed configuration and slidably disposed within an interior lumen of the retrieval assembly, the retrieval device comprising:
      a central shaft extending from a first proximal end to a first distal end defining a first longitudinal axis;
      a plurality of frame struts, each strut of the plurality of frame struts extending from a first end to a second end defining a strut length, the second ends being attached to frame strut attachment points on the central shaft and being disposed radially about the central shaft; and
      a plurality of retraction struts, each strut of the plurality of retraction struts extending from a first connected end to a second connected end, each first connected end being attached to the central shaft at a point proximal to the frame strut attachment points, each second connected end being connected to a frame strut of the plurality of frame struts;
   identifying the location of the intravascular filter using visualization technology;
   advancing the retrieval device still in its collapsed configuration to a retrieval position proximal to the intravascular filter in the body vessel, the retrieval position being distal to a retrieval hook of the intravascular filter;
   expanding the retrieval device into its expanded state;
   engaging the retrieval hook of the intravascular filter with a snare wire of the retrieval device;
   returning the retrieval device, still engaged with the retrieval hook, to its collapsed configuration;
   withdrawing the retrieval device and the intravascular filter into the interior lumen of the retrieval assembly; and
   removing the retrieval assembly and the intravascular filter from the body vessel.

2. The method of claim 1, wherein the second ends of the frame struts are attached to the first distal end of the central shaft and are disposed radially about the central shaft; and
   each first connected end of the plurality of retraction struts is attached to the central shaft distal the first ends of the plurality of frame struts.

3. The method of claim 1, wherein the retrieval device comprises a plurality of snare wires.

4. The method of claim 3, wherein each snare wire of the plurality of snare wires is connected to each of the frame struts at intervals along the strut lengths.

* * * * *